United States Patent [19]

Berneth et al.

[11] Patent Number: 5,292,881

[45] Date of Patent: Mar. 8, 1994

[54] NEW NAPHTHALIMIDES, TONERS CONTAINING THESE AND THE USE OF THE NEW NAPHTHALIMIDES AS ADDITIVES FOR TONERS

[75] Inventors: Horst Berneth, Leverkusen; Horst Harnisch, Muich; Roderich Raue, Leverkusen; Jürgen-Rolf Hassdenteufel, Bergisch Gladbach; Matthias Köcher, Overath, all of Fed. Rep. of Germany

[73] Assignee: Bayer Aktiengesellschaft, Leverkusen, Fed. Rep. of Germany

[21] Appl. No.: 838,129

[22] Filed: Feb. 19, 1992

[30] Foreign Application Priority Data

Feb. 27, 1991 [DE] Fed. Rep. of Germany ....... 4106122

[51] Int. Cl.$^5$ .................. C07D 221/14; C07D 413/06; G03G 9/097; H01F 1/00
[52] U.S. Cl. ..................................... 546/99; 544/126; 430/109
[58] Field of Search ............................ 546/99; 544/126

[56] References Cited

U.S. PATENT DOCUMENTS

| | | | |
|---|---|---|---|
| 4,508,900 | 4/1985 | Schonberger | 546/99 |
| 4,812,379 | 3/1989 | Harnisch et al. | 430/110 |
| 4,841,052 | 6/1989 | Harnisch | 546/99 |
| 4,927,729 | 5/1990 | Harnisch et al. | 546/10 |

FOREIGN PATENT DOCUMENTS

| | | |
|---|---|---|
| 0154740 | 9/1985 | European Pat. Off. . |
| 0233544 | 8/1987 | European Pat. Off. . |
| 3738948 | 5/1989 | Fed. Rep. of Germany . |

OTHER PUBLICATIONS

Iwamoto, Chem Abs 114, 72319f (1990).
Patent Abstracts of Japan vol. 13, No. 505 (P-959) (3853) Nov. 14, 1989 & JP-A-01 202 760 (Tomogawa Paper Co Ltd) Aug. 15, 1989.

*Primary Examiner*—Mark L. Berch
*Attorney, Agent, or Firm*—Sprung Horn Kramer & Woods

[57] ABSTRACT

New naphthalimides, useful as additives in toners for controlling the charge and conductivity, of the formula

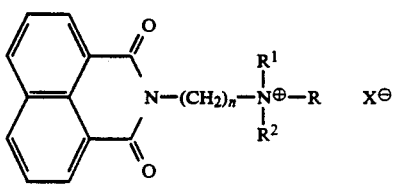

(I)

in which
R represents $C_1$- to $C_{22}$-alkyl,
$R^1$ and $R^2$ independently of one another in each case represent $C_1$- to $C_4$-alkyl, or $R^1$ and $R^2$, together with the nitrogen atom in between, form a pyrrolidine, piperidine or morpholine ring,
n represents 2 or 3 and
$X^\ominus$ represent one equivalent
of a benzoate or naphthoate, which is optionally substituted by chlorine, bromine, methyl, methoxy, hydroxyl, cyano and/or hydroxycarbonyl,
of a benzenesulphonate which is substituted by hydroxyl, amino or nitro,
of a naphthalenesulphonate which is optionally substituted by hydroxyl, amino or a sulphonic acid group, or
of a fluorine-substituted anion of a $C_4$- to $C_{18}$-alkanecarboxylic or -alkanesulphonic acid.

10 Claims, No Drawings

NEW NAPHTHALIMIDES, TONERS CONTAINING THESE AND THE USE OF THE NEW NAPHTHALIMIDES AS ADDITIVES FOR TONERS

The present invention relates to naphthalimides and their use as additives in toners for controlling the charge and conductivity.

Toners are used in the development of electrostatic charge images in electrophotography, electrography and ionography and magnetostatic charge images in magnetography. Of these processes, electrophotography (see, for example, U.S. Pat. No. 2,297,691, U.S. Pat. No. 3,666,363 and U.S. Pat. No. 4,071,361) has acquired the greatest importance.

In this method, a virtual image is generated in the form of electrical charges on a photoconductor by exposure of the original to light or conversion of digitalised image information with the aid of a laser, an LED array or an LCS unit. This charge image is developed by contact with a toner. The toner is in general a powder of pigmented particles which have a defined particle size and defined electrical properties.

The toner which builds up the image is transferred from the surface of the photoconductor to the carrier material (for example paper or film) and fixed there.

The charge image can be developed on the surface of the photoconductor by the one-component process or by the two-component process.

In the two-component process (see, for example, U.S. Pat. No. 2,874,063), toner particles having a size of 5 to 30 $\mu$m and containing 80 to 90% by weight of toner resin, 5 to 15% by weight of pigment and small amounts of additives are charged triboelectrically by mechanical agitation with magnetic carrier particles (for example of pig iron, coated pig iron or ferrites) having a size of 30 to 200 $\mu$m and in this way form a layer on the surface of the oppositely charged carrier particles. The carrier particles are aligned radially on a rotating roll (a so-called magnetic brush) with the aid of a magnetic field and are brought into permanent contact with the similarly rotating photoconductor. The toner particles adhering to the carrier particles are transferred to the oppositely charged areas corresponding to the virtual charge image.

In the one-component process (see, for example, U.S. Pat. No. 3,909,258), carrier-toner hybrid particles are used. These have a size of 5 to 30 $\mu$m and contain 40 to 65% by weight of magnetic pigments, 30 to 60% by weight of toner resin and small amounts of additives. The toner is precharged electrically or triboelectrically and brought onto the surface of a rotating roll spatially close to the photoconductor by a radially aligned magnetic field. The toner particles are transferred to the charged areas corresponding to the virtual charge image.

Flash fixing and hot roll fixing have found acceptance in practice for fixing the toner transferred to the carrier material (for example paper or film).

In flash fixing, the toner is heated up on the carrier material rapidly and without contact, by means of a flash lamp (xenon lamp), so that it fuses into the carrier surface.

In hot roll fixing, the carrier with the adhering toner is brought into contact with a heated roll which bonds the toner permanently to the carrier surface under pressure and heat.

The image quality of the reproduction always depends essentially on the properties of the toner, the electrical properties, in particular the triboelectrical charging and the conductivity, being important for all the transfer processes. It is possible to influence the electrical properties by specific additives (for example so-called charge control substances) or by varying the pigments (for example carbon black).

For a good image quality, the charge level and the conductivity of the toner must be matched exactly to the polarity and initial voltage of the photoconductor, the transfer voltage for transfer to the carrier material and the particular device used (for example copier or laser printer). It must also be ensured that the charges and the conductivities of individual toner particles do not deviate substantially, if at all, from one another.

If the charge is too low or the conductivity is too high, adequate transfer from the magnetic brush to the photoconductor does not take place, the development becomes non-specific (which leads to blurring) and the transfer onto the carrier material becomes inadequate (accumulation of so-called "waste toner").

If the charge is too high, the transfer processes are greatly impeded because of pronounced adhesion of the toner powder to the magnetic brush and to the photoconductor, and they are not adequately effective.

If the toner powder contains particles of different charge level, particles of higher charge are preferentially transferred and particles of low charge become concentrated in toner which has not yet been transferred. This results in an inadequate performance over a long operating period. Particles of reversed polarity (so-called "wrong sign particles") are extremely troublesome.

For trouble-free progress of electrophotographic processes, it is also necessary for the charge level and the conductivity of the toner particles to be as independent as possible of climatic influences, for example of temperature and atmospheric humidity.

Attempts are made to impart the desired properties to toners by adding to them so-called charge control substances, for example 1 to 3% by weight of specific ammonium or pyridinium salts, metal complexes and/or specific pigments (see U.S. Pat. Nos. 3,893,935, 3,944,493, 4,007,293, 4,079,014, 4,298,672, 4,338,390, 4,394,439 and 4,493,883 and German offenlegungsschrift 3,604,827).

A procedure can be followed here in which, for example, 5 to 15% by weight of customary pigments, 0.5 to 3% by weight of charge control substances and if appropriate other additives (for example 1 to 3% by weight of polyolefin waxes to increase the adhesive properties) are kneaded into the resin, the mixture is then finely ground and subsequently subjected to several sifting steps to establish a defined particle size, and the desired powder flow properties are finally established using highly disperse silicic acid or similar products.

The uniformity of the individual toner particles is of the greatest importance for the quality of the toner thus obtained. High requirements are therefore imposed on the dispersibility of the additives, in particular the charge control substances.

The charge control substances used furthermore should not undergo chemical interactions with components of the equipment (for example the photoconductor or fixing roll) which would lead to irreversible soiling of and damage to the components affected. A high heat stability of the charge control substances is required here, especially in respect of the heated fixing rolls.

In addition to these diverse requirements of charge control substances, these must have a good transparency and as far as possible only a slight intrinsic colour, or preferably none at all, for production of coloured photocopies and coloured image reproductions.

The charge control substances described in German Offenlegungsschrift 3,604,827 have proved to be usable, but their chargeability, their long-term stability and their insensitivity to atmospheric humidity are still not completely satisfactory.

Naphthalimides of the formula (I)

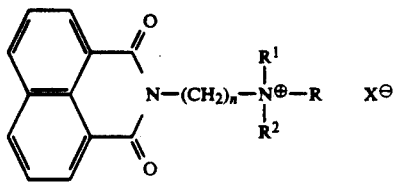

in which
R represents $C_1$- to $C_{22}$-alkyl,
$R^1$ and $R^2$ independently of one another in each case represent $C_1$- to $C_4$-alkyl, or $R^1$ and $R^2$, together with the nitrogen atom in between, form a pyrrolidine, piperidine or morpholine ring,
n represents 2 or 3 and
$X^\ominus$ represents one equivalent
of a benzoate or naphthoate, which is optionally substituted by chlorine, bromine, methyl, methoxy, hydroxyl, cyano and/or hydroxycarbonyl,
of a benzenesulphonate which is substituted by hydroxyl, amino or nitro,
of a naphthalenesulphonate which is optionally substituted by hydroxyl, amino or a sulphonic acid group, or
of a fluorine-substituted anion of a $C_4$- to $C_{18}$-alkanecarboxylic or -alkanesulphonic acid,
have now been found.

In preferred naphthalimides of the formula (I), R represents $C_4$- to $C_{16}$-alkyl and/or $R^1$ and $R^2$ represent methyl or ethyl and/or n represents 3 and/or $X^\ominus$ represents one equivalent of a benzoate, benzenesulphonate or naphthalenesulphonate.

Of the fluorine-substituted anions of $C_4$- to $C_{18}$-alkanecarboxylic and -alkanesulphonic acids, those of alkanesulphonic acids having 4 to 12 C atoms are preferred.

Up to three identical or different substituents of those mentioned for benzoate, naphthoate, benzenesulphonate and naphthalenesulphonate can be present simultaneously.

Examples of anions $X^\ominus$ are: benzoate, 2-, 3- and 4-chlorobenzoate, 2-, 3- and 4-bromobenzoate, salicylate, 4-hydroxybenzoate, 3-hydroxybenzoate, phthalate, isophthalate, terephthalate, 2-, 3- and 4-nitrobenzoate, 2-, 3- and 4-cyanobenzoate, 2-, 3- and 4-methylbenzoate, 2-, 3-and 4-methoxybenzoate, 2-hydroxy-3-, 2-hydroxy-4-and 2-hydroxy-5-methylbenzoate, 5-chlorosalicylate, 2,3-, 2,4-and 3,5-dihydroxybenzoate, the anions of 2-hydroxynaphthalene-1-carboxylic acid, 1-hydroxynaphthalene-2-carboxylic acid and 2-hydroxynaphthalene-3-carboxylic acid, 4-hydroxyphthalate, 2,5- and 4,6-dihydroxyiso- and -terephthalate, 2-, 3- and 4-aminobenzoate, 2-amino-4-and 2-amino-6-chlorobenzoate, 3-, 4- and 5-amino-2hydroxybenzoate, phenol-2-, -3- and -4-sulphonate, aminobenzene-2-, -3- and -4-sulphonate, nitrobenzene-2-, -3- and -4-sulphonate, 4-nitrophenol-2-sulphonate, naphthalene-1- and -2-sulphonate, 1-hydroxynaphthalene-2-, -3-, -4-, -6-, -7- and -8-sulphonate, 2-hydroxynaphthalene-1-, -4-, -5- and -6-sulphonate, 1-aminonaphthalene-4- and -8-sulphonate, 2-aminonaphthalene-1-sulphonate, 1-hydroxynaphthalene-3,6- and -3,8-disulphonate, 1,6- and 1,7-dihydroxynaphthalene-3-sulphonate, 1-aminonaphthalene-3,8-disulphonate, 2-aminonaphthalene-6,8-disulphonate, 6- and 7-amino-1-hydroxynaphthalene-3-sulphonate, 1-amino-8-hydroxynaphthalene-2,4-, -3,6- and -4,6-disulphonate, perfluorobutane-1-sulphonate and perfluorooctane-1-sulphonate.

Examples of the radical R are straight-chain, branched and cyclic alkyl radicals, such as methyl, ethyl, 1- and 2-propyl, 1- and 2-butyl, 1- and 2-pentyl, 1- and 2-hexyl, 1-octyl, 1-decyl, 1-dodecyl, 2-ethyl-1-hexyl, 1-tetradecyl, 1-hexadecyl, 1-octadecyl, cyclohexyl and cyclopentyl.

The present invention furthermore relates to toners which contain one or more naphthalimides of the formula (I) as an additive which increases the positive charge. Such toners can contain, for example, 0.5 to 3% by weight of these naphthalimides, and can otherwise have the customary composition. For example, such toners can contain 40 to 90% by weight of toner resin, 4 to 10% by weight of pigments, for example carbon black, 0.5 to 5% by weight of polyolefins and if appropriate 30 to 60% by weight of magnetic pigments.

Finally, the present invention also relates to the use of naphthalimides of the formula (I) as an additive which increases the positive charge of toners.

Positive charge control substances which are comparable in their chemical structure are known from German Offenlegungsschrift 3,604,827. Compared with the charge control substances described in that specification, the naphthalimides of the present invention essentially contain different anions. In addition to all the advantages mentioned in German Offenlegungsschrift 3,604,827, the naphthalimides according to the invention surprisingly display a considerably higher charging, a better long-term stability in the equipment test and a higher insensitivity to atmospheric humidity.

The naphthalimides according to the invention can be prepared by methods which are known per se, for example by processes analogous to those described in German Offenlegungsschriften 3,535,496 and 3,604,827. The most diverse anions $X^\ominus$ can be produced, for example, by anion exchange with the corresponding bromide. In this procedure, $X^\ominus$ can be introduced, for example, in the form of the corresponding acid or the corresponding alkali metal salts or ammonium salts.

EXAMPLES

Example 1

194.4 g of 1-amino-3-dimethylaminopropane were added dropwise at 80° C. to 375 g of naphthalic anhydride in 2,355 g of isopropanol and 2.7 g of glacial acetic acid. After 2 hours, 63 g of sodium bicarbonate were introduced, and 762.3 g of 1-bromohexadecane were added dropwise at 70° C. After the mixture had been boiled for 15 hours, the solvent was distilled off up to a bottom temperature of 105° C., and after the residue had been cooled to 60° C., 2,370 g of acetone were added.

on cooling, 918 g (82.5% of theory) of the bromide, which corresponded to the formula (I) where $R=C_{16}H_{33}$ and $X^\ominus=Br^\ominus$, crystallised out.

293.8 g of this bromide were suspended in 2,500 ml of water, and 216 g of sodium benzoate were introduced. After the mixture had been stirred overnight, 306.4 g (97.5% of theory) of pale beige crystals of melting point 89° to 91° C., which corresponded to the formula (I) where $R=C_{16}H_{33}$ and $X^\ominus=$ unsubstituted benzoate, were obtained.

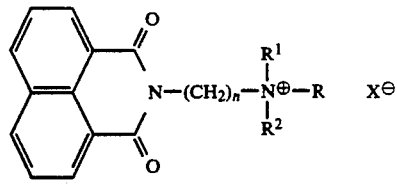

(I)

Unless stated otherwise, $R^1=R^2=$ methyl and $n=3$.

TABLE 1

| Example No. | analogously to Example | R | $X^\theta$ | Melting point (°C.) |
| --- | --- | --- | --- | --- |
| 3 | 1 | $C_{16}H_{33}$ | 2-hydroxybenzoate | 133 to 135 |
| 4 | 1 | $C_{16}H_{33}$ | phthalate | 162 to 164 |
| 5 | 1 | $C_{16}H_{33}$ | 1-sulphonato-2-hydroxynaphthalene | 184 to 187 |
| 6 | 2 | $C_{16}H_{33}$ | 1-hydroxy-3-sulphonato-6-aminonaphthalene | 158 to 161 |
| 7 | 1 | $C_4H_9$ | 4-hydroxybenzoate | 112 to 115 |
| 8 | 1 | $C_{22}H_{34}$ | 4-chlorobenzoate | 68 to 72 |
| 9  $R^1 = R^2 =$ ethyl | 1 | $C_{16}H_{33}$ | 1-hydroxy-4-sulphonato-naphthalene | |
| 10 | 2 | $C_{16}H_{33}$ | 3-nitrobenzoate | 76 to 77 |
| 11 | 2 | $C_{16}H_{33}$ | 4-methoxybenzoate | |
| 12 | 1 | $C_8H_{17}$ | 2-hydroxy-3-methyl-benzoate | 74 to 75 |
| 13 | 2 | $C_8H_{17}$ | 2-aminobenzoate | |
| 14 | 1 | $C_{12}H_{25}$ | 2-hydroxybenzenesulphonate | |
| 15 | 1 | $C_{16}H_{33}$ | 2-hydroxy-4-aminobenzene-sulphonate | 163–165 |
| 16  $R^1 = R^2 =$ butyl | 1 | $C_{16}H_{33}$ | 6-sulphonato-2-hydroxynaphthalene | |
| 17 | 1 | $C_{16}H_{33}$ | 3-sulphonato-1,7-dihydroxynaphthalene | 125–127 |
| 18 | 1 | $C_{16}H_{33}$ | 6-sulphonato-1-amino-naphthalene | |
| 19 | 2 | $C_{16}H_{33}$ | 6-sulphonato-2-amino-naphthalene | |
| 20  $N(R^1)(R^2) =$ morpholine,  $n = 2$ | 1 | $C_4H_9$ | 1-amino-3-sulphonato-8-hydroxy-6-naphthalene-sulphonic acid | |
| 21 | 1 | $C_{14}H_{29}$ | 1,8-dihydroxy-3-sulphonato-6-naphthalenesulphonic acid | |
| 22 | 2 | $C_{16}H_{33}$ | perfluorobutanesulphonate | 202–203 |
| 23 | 1 | $C_{16}H_{33}$ | perfluorooctanesulphonate | |
| 24  $N(R^1)(R^2) =$ piperidine | 1 | $C_{16}H_{33}$ | 2-hydroxybenzoate | |

Example 2

5.9 g of the bromide from Example 1 were suspended in 50 ml of ethanol, and 1.2 g of propylene oxide (to remove $Br^\ominus$) and 4.2 g of naphthalene-2-sulphonic acid were added.

After the mixture had been stirred for 2 hours, it was filtered with suction, and the residue was washed with ethanol. 6.4 g (89% of theory) of a pale beige crystalline powder, which corresponded to the formula (I) where $R=C_{16}H_{33}$ and $X^\ominus=$ unsubstituted naphthalene-2-sulphonate, were obtained. The crystals had a melting point of 195 to 200° C.

Examples 3 to 24

The following compounds were prepared analogously to Examples 1 or 2:

Example 25 (toner example)

90 g of styrene/butyl methacrylate copolymer were kneaded at 150° C. with 7 g of carbon black and 3 g of the naphthalimide derivative obtained according to Example 4. After comminution, coarse prelimindry grinding and subsequent grinding in a jet mill, a toner having a article size $d_{50}$ of 13 μm was obtained by sifting. The triboelectric charging against a soft iron carrier was 20.5 μC/g. It was influenced hardly at all by the atmospheric humidity. No decrease in the charge was found in the long-term equipment test.

The naphthalimide derivatives of Examples 1–3 and 5–24 also have similarly good properties.

Example 26 (comparison example)

A toner was prepared as in Example 25, but a naphthalimide derivative which differed from that of Example 4 in that, instead of a phthalate anion, it contained a bromide anion, as is known from German Offenlegungsschrift 3,604,827, was used.

The toner exhibited a lower initial charge of 15 μC/g. The triboelectric charging against a soft iron carrier decreased to 5 μC/g after agitation with a soft iron carrier for 10 hours. Analogous phenomena were found in the equipment test.

Example 27 (comparison example)

A toner was prepared as in Example 25, but a naphthalimide derivative which differed from that of Example 4 in that, instead of a phthalate anion, it contained a hydrogen sulphate anion, as is known from German Offenlegungsschrift 3,604,827, was used. The toner exhibited a lower initial charge of 14.5 μC/g, which decreased to 7 μC/g after agitation with a soft iron carrier for 10 hours. Analogous phenomena were found in the equipment test.

Examples 28 to 32 (toner examples)

The following toners were prepared analogously to the toner preparation according to Example 25 and were tested as described in Example 25:

TABLE 2

| Example No. | Naphthalimide from Example No. | Charge (μC/g) |
| --- | --- | --- |
| 28 | 3 | 19.7 |
| 29 | 5 | 17.9 |
| 30 | 6 | 16.9 |
| 31 | 9 | 18.5 |
| 32 | 7 | 17.8 |

Example 33 (toner example)

90 g of styrene/butyl acrylate copolymer were kneaded at 150° C. with 7 g of carbon black, 3 g of polypropylene and 1.8 g of the naphthalimide derivative obtained according to Example 4. After comminuation, coarse preliminary grinding and subsequent grinding in a jet mill, a toner having a particle size $d_{50}$ of 13 μm was obtained by sifting. The triboelectric charging against a ferrite carrier was 27.8 μC/g. It was influenced hardly at all by the atmospheric humidity. No decrease in the charge was found in the long-term equipment test.

The naphthalimide derivatives of Examples 1-3 and 5-24 also have similarly good properties.

Example 34 (comparison example)

A toner was prepared as in Example 33, but a naphthalimide derivative which differed from that of Example 4 in that, instead of the phthalate anion, it contained a bromide anion, as is known from German Offenlegungsschrift 3,604,827, was used.

The toner exhibited a lower initial charge of 17 μC/g. The triboelectric charging against a soft iron carrier decreased to 3 μC/g after agitation with a ferrite carrier for 10 hours. Analogous phenomena were found in the equipment test.

Example 35 (comparison example)

A toner was prepared as in Example 33, but a naphthalimide derivative which differed from that of Example 4 in that, instead of a phthalate anion, it contained a hydrogen sulphate anion, as is known from German Offenlegungsschrift 3,604,827, was used. The toner exhibited a lower initial charge of 11.7 μC/g, which decreased to 5 μC/g after agitation with a ferrite carrier for 10 hours. Analogous phenomena were found in the equipment test.

Examples 36–40

Toner preparations were prepared and tested analogously to Example 33. For the results, see Table 3.

TABLE 3

| Example No. | Naphthalimide No. | Charge (μC/g) |
| --- | --- | --- |
| 36 | 3 | 25.2 |
| 37 | 5 | 23.4 |
| 38 | 6 | 27.3 |
| 39 | 9 | 27.9 |
| 40 | 7 | 33.2 |

What is claimed is:

1. naphthalimides of the formula (I)

$$\text{(I)}$$

in which

R represents $C_1$- to $C_{22}$-alkyl, $R^1$ and $R^2$ independently of one another in each case represent $C_1$- to $C_4$-alkyl, or $R^1$ and $R^2$, together with the nitrogen atom in between, form a pyrrolidine, piperidine or morpholine ring, n represents 2 or 3 and $X^\ominus$ represent one equivalent of nitrobenzoate or of a benzoate or naphthoate, which is optionally substituted by chlorine, bromine, methyl, methoxy, hydroxyl, cyano cyano and/or hydroxycarbonyl, of a naphthalenesulphonate which is optionally substituted by amino or a sulphonic acid group, or of a fluorine-substituted anion of a $C_4$- to $C_{18}$-alkanecarboxylic or -alkanesulphonic acid.

2. Naphthalimides of claim 1, in which in formula (I) R represents $C_4$- to $C_{16}$-alkyl.

3. Naphthalimides of claim 1, in which $R^1$ and $R^2$ represent methyl or ethyl.

4. Naphthalimides of claim 1, in which n represents 3.

5. Naphthalimides of claim 1, in which $X^\ominus$ represents one equivalent of a benzoate, benzenesulphonate or naphthalenesulphonate.

6. Naphthalimides of claim 1, in which in formula (I) $X^\ominus$ represents one equivalent of a fluoroalkanesulphonic acid having 4 to 12 C atoms.

7. Naphthalimides of the formula (I)

$$\text{(I)}$$

in which

R represents $C_1$- to $C_{22}$-alkyl, $R^1$ and $R^2$ independently of one another in each case represent $C_1$- to $C_4$-alkyl, or $R^1$ and $R^2$, together with the nitrogen atom in between, form a pyrrolidine, piperidine or morpholine ring, n represents 2 or 3 and $X^\ominus$ represent on equivalent of a benzoate or naphthoate, which is optionally substituted by chlorine, bromine, methyl, methoxy, hydroxyl, cyano and/or hydroxycarbonyl, of a benzenesulphonate which is substituted by amino or nitro, of a naphthalensesulphonate which is optionally substituted by amino or a sulphonic acid group, or of a fluorine-substituted anion of a $C_4$- to $C_{18}$-alkanecarboxylic or -alkanesulphonic acid wherein two to three identical or different substituents of those mentioned for benzoate, naphthoate, benzene sulphonate and naphthenesulphonate are present simultaneously.

8. Naphthalimides of claim 1, in which in formula (I) $X^\ominus$ represents benzoate, 2-, 3- and 4-chlorobenzoate, 2-, 3- or 4-bromobenzoate, salicylate, 4-hydroxybenzoate, 3-hydroxybenzoate, phthalate, isophthalate, terephthalate, 2-, 3- or 4-nitrobenzoate, 2-, 3- or 4-cyanobenzoate, 2-, 3- or 4-methylbenzoate, 2-, 3- or 4-methoxybenzoate, 2-hydroxy-3-, 2-hydroxyl-4- or 2-hydroxy-5-methylbenzoate, 5-chlorosalicylate, 2,3-, 2,4-or 3,5-dihydroxybenzoate, the anions of 2-hydroxynaphthalene-1-carboxylic acid, 1-hydroxynaphthalene-2-carboxylic acid or 2-hydroxynaphthalene-3-carboxylic acid, 4-hydroxyphthalate, 2,5- or 4,6-dihydroxyiso- or -trephthalate, 2-, 3- and 4-aminobenzoate, 2-amino-4-or 2-amino-6-chlorobenzoate, 3-, 4- or 5-amino-2-hydroxybenzoate, aminobenzene-2-, -3- or -4-sulphonate, nitrobenzene-2-, -3- or -4-sulphonate, naphthalene-1- and -2-sulphonate, 1-aminonaphthalene-4- or -8-sulphonate, 2-aminonaphthalene-1-sulphonate, 1-aminonaphthalene-3,8-disulphonate, 2-aminonaphthalene-6,8-disulphonate, 6- or 7-amino-1-hydroxynaphthalene-3-sulphonate, 1-amino-8-hydroxynaphthalene-2,4-, -3,6- or -4,6-disulphonate, perfluorobutane-1-sulphonate or perfluorooctane-1-sulphonate.

9. Naphthalimides of claim 1, in which in formula (I) R represents one of methyl, ethyl, 1- and 2-propyl, 1-and 2-butyl, 1- and 2-pentyl, 1-and 2-hexyl, 1-octyl, 1-decyl, 1-dodecyl, 2-ethyl-1-hexyl, 1-tetradecyl, 1-hexadecyl, 1-octadecyl, cyclohexyl and cyclopentyl.

10. Naphthalimides of claim 1, in which $X^\ominus$ represents one equivalent of a benzoate or naphthoate, which is optionally substituted by chlorine, bromine, methyl, methoxy, hydroxyl, cyano and/or hydroxycarbonyl, of a benzenesulphonate which is substituted by amino or nitro, or of a fluorine-substituted anion of a $C_4$- to $C_{18}$-alkanecarboxylic or -alkanesulphonic acid.

* * * * *